US008986936B2

(12) United States Patent
Pinet et al.

(10) Patent No.: US 8,986,936 B2
(45) Date of Patent: Mar. 24, 2015

(54) POST-TRANSLATION MODIFIED CARDIAC TROPONIN T AS A BIOMARKER OF A RISK FOR HEART FAILURE

(75) Inventors: Florence Pinet, Lille Cedex (FR); Paul Mulder, Rouen Cedex (FR); Christophe Bauters, Lille Cedex (FR); Vincent Richard, Rouen Cedex (FR)

(73) Assignees: Inserm (Institut National de la Santa et de la Recherche Medicale), Paris (FR); Institute Pasteur de Lille, Lille (FR); Le Centre Hospitalier Regional Universitaire de Lille, Lille Cedex (FR); Universite de Rouen, Mont-Saint-Aignan (FR)

( * ) Notice: Subject to any disclaimer, the term of this patent is extended or adjusted under 35 U.S.C. 154(b) by 499 days.

(21) Appl. No.: 13/321,601

(22) PCT Filed: May 20, 2010

(86) PCT No.: PCT/EP2010/056931
§ 371 (c)(1),
(2), (4) Date: Dec. 27, 2011

(87) PCT Pub. No.: WO2010/133655
PCT Pub. Date: Nov. 25, 2010

(65) Prior Publication Data
US 2012/0088259 A1    Apr. 12, 2012

(30) Foreign Application Priority Data

May 22, 2009   (EP) ..................... 09305471

(51) Int. Cl.
*G01N 33/53*    (2006.01)
*A61K 38/16*    (2006.01)
*G01N 33/68*    (2006.01)

(52) U.S. Cl.
CPC .... *G01N 33/6887* (2013.01); *G01N 2333/4712* (2013.01); *G01N 2800/325* (2013.01); *Y10S 436/811* (2013.01)
USPC ........... 435/7.1; 435/7.92; 436/517; 436/518; 436/548; 436/35; 436/172; 436/811; 530/352

(58) Field of Classification Search
USPC ............ 435/7.1, 7.92; 436/517, 518, 548, 35, 436/172, 811; 530/352
See application file for complete search history.

(56) References Cited

U.S. PATENT DOCUMENTS 7,618,782 B1 * 11/2009 Van Eyk et al. ................ 435/7.1
2004/0175754 A1 * 9/2004 Bar-Or et al. .................. 435/7.1

OTHER PUBLICATIONS

"Abstracts from the 2009 Annual Meeting of the International Society for Heart Research North American Selection," J. Mol. Cell. Cardiol., 46(5):S1-S55 (2009) XP026090504.
Anderson et al., "Troponin T isoform expression in humans. A comparison among normal and failing adult heart, fetal heart, and adult and fetal skeletal muscle," Circ. Res., 69(5):1226-1233 (1991) XP002542292.
Atar et al., "[Molecular modifications of troponin I and T detected in serum from patients with acute myocardial infarction]" Ugeskr. Laeger, 165(2):116-120 (2003) XP008114053.

(Continued)

Primary Examiner — Gail R Gabel
(74) Attorney, Agent, or Firm — McAndrews Held & Malloy

(57) ABSTRACT

The present invention relates to methods and kits for the prediction of risk for heart failure using post-translation modified forms of cardiac troponin T as a biomarker.

2 Claims, 3 Drawing Sheets

Phosphorylated-Ser$^{207}$-troponin T

(56) References Cited

OTHER PUBLICATIONS

International Search Report and Written Opinion in PCT/EP2010/056931, dated Aug. 11, 2010.

Kameyama et al., "Mechanoenergetic alterations during the transition from cardiac hypertrophy to failure in Dahl salt-sensitive rats," Circulation, 98(25):2919-2929 (1998) XP002542291.

Li et al., "Myocardial infarction affects myofilament responsiveness to calcium, mechanical characteristics of myocytes and the phosphorylation of troponin 1 and troponin T," Circulation, 94(8 Suppl):I724 (1996) XP008114052.

Li et al., "Myocardial infarction alters myofilament calcium sensitivity and mechanical behavior of myocytes," Am. J. Physiol., 272(1 Pt 2):H360-H370 (1997) XP008114063.

Marston et al., "Troponin phosphorylation and myofilament $Ca^{2+}$-sensitivity in heart failure: Increased or decreased?" J. Mol. Cell. Cardiol., 45(5):603-607 (2008) XP025662940.

Metzler et al., "Mouse model of myocardial remodelling after ischemia: Role of intercellular adhesion molecule-1," Cardiovasc. Res., 49(2):399-407 (2001) XP002542296.

Noguchi et al., "Altered myocardial thin-filament function in the failing Dahl salt-sensitive rat heart: Amelioration by endothelin blockade," Circulation, 107(4):630-635 (2003) XP002542290.

Walker et al., "Stage-specific changes in myofilament protein phosphorylation following myocardial infarction," Circulation Res., 103(5):E46 (2008) XP002552621.

* cited by examiner

POST-TRANSLATION MODIFIED CARDIAC TROPONIN T AS A BIOMARKER OF A RISK FOR HEART FAILURE

The present application is filed pursuant to 35 U.S.C. 371 as a U.S. National Phase application of International Patent Application No. PCT/EP2010/056931, which was filed May 20, 2010, claiming the benefit of priority to European Patent Application No. 09305471.6, which was filed on May 22, 2009. The entire text of the aforementioned applications is incorporated herein by reference in its entirety.

FIELD OF THE INVENTION

The present invention provides new biomarkers for the detection of left ventricular remodelling and the management and the appreciation of risk for heart failure. Accordingly, the invention provides methods and kits of the detection of left ventricular remodelling and the prediction of risk for heart failure.

BACKGROUND OF THE INVENTION

Heart failure is today a major health problem that affects more than five millions people in US and accounts for about 500,000 new cases each year and its prevalence is steadily increasing. It consists in a condition in which a problem with the structure or function of the heart impairs its ability to supply sufficient blood flow to meet the body's needs.

This pathology is caused by different factors and results for several complex mechanisms. For the clinical management of this serious disorder, the finding of new biomarkers and therapeutic targets appear to have a growing importance. Particularly, for an easier monitoring, research now focuses on serum biomarkers.

An increasing number of enzymes, hormones, biological substances and other markers of cardiac system are used as biomarker of cardiac disorders such as heart failure. Currently, among biomarkers used for the management of heart failure after myocardial infarction appear serum troponin T (Newby L K et al, 1998; Latini R et al, 2007) and troponin I, B-type natriuretic peptide (BNP) and C-reactive protein (CRP). These biomarkers assess different pathways that have been implicated in the pathogenesis of heart failure: BNP is elevated in response to left ventricular overload; CRP is a marker of inflammation; and elevations in troponin indicate myocyte injury.

However, there is still a need of new biomarkers for the management of heart failure, for an earlier detection or appreciation of risk for such disorder and easier tests.

Left ventricular remodeling after myocardial infarction is observed in approximately 30% of patients despite modern therapeutic strategies. Initially, left ventricular remodeling can be considered as a protective mechanism maintaining cardiac pump function, but ultimately it leads to deterioration in global left ventricular function and to heart failure. Since myocardial infarction is a frequent event (120 000 cases/year in France), left ventricular remodeling is an important contributor to the current epidemic of heart failure. The discovery of circulating markers specific to remodeling would allow for the development of biological tests predicting a development to heart failure.

SUMMARY OF THE INVENTION

The present invention relates to an in vitro method for detecting a post-infarction left ventricular remodelling in a subject, said method comprising the steps of:

(i) measuring the level of phosphorylated troponin T in the troponin T pool in a blood sample obtained from the subject,
(ii) comparing said level to a control,
(iii) wherein a decreased level of phosphorylated troponin T in the blood sample is indicative of a left ventricular remodelling.

The present invention also relates to an in vitro method for predicting the risk of heart failure in a subject who had an infarction, said method comprising the steps of:

(i) measuring the level of phosphorylated troponin T in the troponin T pool in a blood sample obtained from the subject,
(ii) comparing said level to a control,
(iii) wherein a decreased level of phosphorylated troponin T in the blood sample is indicative of a high risk of heart failure.

The present invention further relates to an in vitro method for predicting the risk of heart failure in a subject who had no infarction, said method comprising the steps of:

(i) measuring the level of phosphorylated troponin T in the troponin T pool in a blood sample obtained from the subject,
(ii) comparing said level to a control,
(iii) wherein an increased level of phosphorylated troponin T in the blood sample is indicative of a high risk of heart failure.

Accordingly, the invention relates to the use of phosphorylated troponin T as a biomarker of the risk of heart failure in a subject and provides kits for use in the methods of the invention.

BRIEF DESCRIPTION OF THE DRAWINGS

FIG. 1: Decrease of human $Ser^{207}$-phosphorylated TnT in plasma of patients with LV remodeling after MI.

DETAILED DESCRIPTION OF THE INVENTION

Figure 1A:
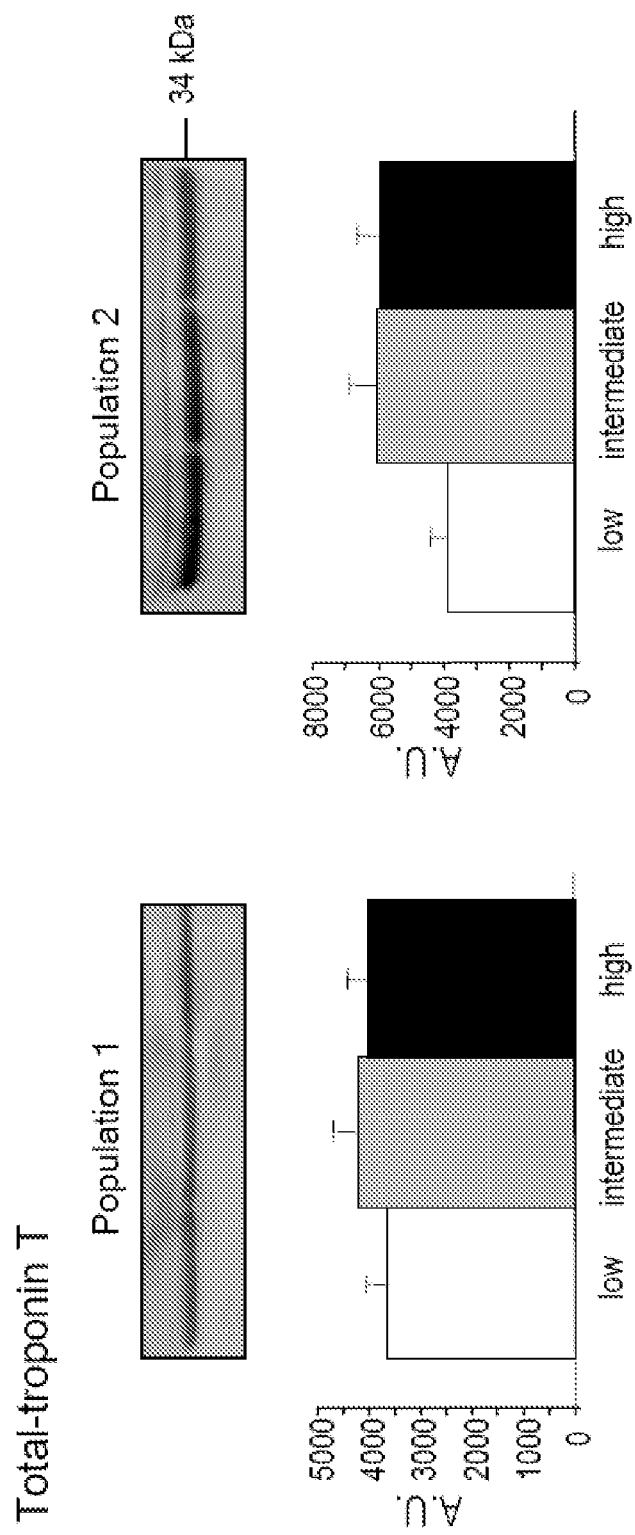
FIG. 1A depicts western blot analysis with antibodies against total human TnT in plasma (1 µL) from patients.

The inventors have shown that post-translational modified troponin T, and more particularly phosphorylated troponin T, is a biomarker of left ventricular remodelling, a post-infarction process leading to heart failure. Indeed, the level of phosphorylation is decreased in case of left ventricular remodelling. Furthermore, the level of glycosylation of troponin T has also been studied and is increased in case of left ventricular remodelling. Accordingly, post-translational modified troponin T can be used as a biomarker of risk of heart failure in a subject who had an infarction.

The inventors also showed that post-translational modified troponin T, and more particularly phosphorylated troponin T, can be used as a biomarker of heart failure in a subject who had no infarction. But surprisingly, the inventors have shown that an increase of the level of phosphorylation and/or a decrease of the level of glycosylation are correlated to a risk of heart failure in a subject who had no infarction.

Thus, post-translational modified troponin T can be used as a biomarker of heart failure in subjects who had or not an infarction, and as a biomarker of post-infarction left ventricular remodelling.

DEFINITIONS

The term "Troponin T" (TnT) has its general meaning in the art and refers to the cardiac form of troponin T, a myofibrillar protein already used as a biomarker of cardiac disorders. The term may include naturally occurring cardiac troponin T and variants and modified forms thereof. The cardiac troponin T can be from any source, but typically is a mammalian (e.g., human and non-human primate) cardiac troponin T, particularly a human cardiac troponin T. An exemplary human native cardiac troponin T amino acid sequence is provided in P45359 (Swiss-Prot database) and an exemplary rat native amino acid sequence is provided in P50753 (Swiss-Prot database).

According to the invention, the term "phosphorylated troponin T" refers to a particular form of the troponin T which is phosphorylated on a serine. Namely, the human protein is phosphorylated on serine 207 (see position 207 of P45379 (1-297 aa)) and the rat protein is phosphorylated on the serine 208 (see position 208 of P50753 (1-298 aa)), taking account of the removing of initiator methionine (UniProtKB/Swiss-Prot Release 57.1 of 14 Apr. 2009: 412525 entries).

According to the invention, the term "glycosylated troponin T" refers to a particular form of troponin T which is glycosylated with a monosaccharide, β-N-acetylglucosamine, which is an O-glycosidic linkage termed O-GlcNAc.

According to the invention, the term "troponin T pool" relates to the whole forms of troponin T contained in the biological sample obtained from the subject, that can be post-translational modified or not. Thus, the pool includes non modified troponin T, phosphorylated troponin T and glycosylated troponin T.

The terms "biomarker" and "marker" are used herein interchangeably. They refer to a substance that is a distinctive indicator of a biological process, biological event, and/or pathologic condition.

As used herein, the term "subject" refers to a human or another mammal (e.g., primate, dog, cat, goat, horse, pig, mouse, rat, rabbit, and the like), that can be afflicted with heart failure, but may or may not have the disease. In a particular embodiment of the present invention, the subject is a human. In particular, the subject can be a patient.

The term "biological sample" is used herein in its broadest sense. A biological sample is generally obtained from a subject. A sample may be of any biological tissue or fluid with which biomarkers of the present invention may be assayed. Frequently, a sample will be a "clinical sample", i.e., a sample derived from a patient. Such samples include, but are not limited to, bodily fluids which may or may not contain cells, e.g., blood (e.g., whole blood, serum or plasma). The term "biological sample" also encompasses any material derived by processing a biological sample. Derived materials include, but are not limited to, cells (or their progeny) isolated from the sample or proteins extracted from the sample. Processing of a biological sample may involve one or more of: filtration, distillation, extraction, concentration, inactivation of interfering components, addition of reagents, and the like.

According to the invention, the biological sample is a blood sample (whole blood, serum or plasma).

The terms "normal" and "healthy" are used herein interchangeably. They refer to a subject that has not shown any cardiovascular symptoms, and that has not been diagnosed with heart failure or with other cardiovascular disease. Preferably, a normal subject is not on medication affecting cardiovascular system and has not been diagnosed with any other disease. In certain embodiments, normal subjects have similar sex, age, and/or body mass index as compared with the subject from which the biological sample to be tested was obtained. The term "normal" is also used herein to qualify a sample obtained from a healthy subject.

In the context of the present invention, the term "control", when used to characterize a subject, refers to a subject that is healthy or to a patient that has been diagnosed with a specific disease other than cardiovascular disease. The term "control sample" refers to one, or more than one sample, that has been obtained from a healthy subject or from a patient diagnosed with a disease other than cardiovascular disorder.

In its broadest meaning, the term "preventing" or "prevention" refers to preventing the disease or condition from occurring in a subject which has not yet been diagnosed as having it.

In its broadest meaning, the term "treating" or "treatment" refers to reversing, alleviating, inhibiting the progress of the disorder or condition to which such term applies, or one or more symptoms of such disorder or condition.

The term "pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

PREDICTIVE METHODS OF THE INVENTION

The first object of the present invention relates to an in vitro method for detecting a post-infarction left ventricular remodelling in a subject, said method comprising the steps of:
  (i) measuring the level of phosphorylated troponin T in the troponin T pool in a blood sample obtained from the subject,
  (ii) comparing said level to a control,
  (iii) wherein a decreased level of phosphorylated troponin T in the blood sample is indicative of a left ventricular remodelling.

In a particular embodiment, said method can further comprise the steps of:
  (iv) measuring the level of glycosylated troponin T in the troponin T pool in said sample,
  (v) comparing said level to a control,
  (vi) wherein an increased level of glycosylated troponin T in said sample is indicative of a left ventricular remodelling.

Left ventricular remodelling is a complex post-infarction process occurring in about 30% of cases that leads to heart failure at long term.

Thus, a further object of the invention relates to an in vitro method for predicting the risk of heart failure in a subject who had an infarction, said method comprising the steps of:

(i) measuring the level of phosphorylated troponin T in the troponin T pool in a blood sample obtained from the subject,
(ii) comparing said level to a control,
(iii) wherein a decreased level of phosphorylated troponin T in the blood sample is indicative of a high risk of heart failure.

In a particular embodiment, the method can further comprise the steps of:
(iv) measuring the level of glycosylated troponin T in the troponin T pool in said blood sample,
(v) comparing said level to a control,
(vi) wherein an increased level of glycosylated troponin T in said sample is indicative of a high risk of heart failure.

According to the invention, the level of phosphorylated troponin T corresponds to the ratio of phosphorylated troponin T to total troponin T as well as the level of glycosylated troponin T corresponds to the ratio of glycosylated troponin T to total troponin T.

Typically, a decreased level of phosphorylated troponin T corresponds to 50% or less of the level measured in a control sample.

Another object of the invention relates to an in vitro method for predicting the risk of heart failure in a subject who had no infarction, said method comprising the steps of:
(i) measuring the level of phosphorylated troponin T in the troponin T pool in a blood sample obtained from the subject,
(ii) comparing said level to a control,
(iii) wherein an increased level of phosphorylated troponin T in the blood sample is indicative of a high risk of heart failure.

In a particular embodiment, the method can further comprise the steps of:
(iv) measuring the level of glycosylated troponin T in the troponin T pool in said blood sample,
(v) comparing said level to a control,
(vi) wherein a decreased level of glycosylated troponin T in said sample is indicative of a high risk of heart failure.

According to the invention, the level of phosphorylated troponin T corresponds to the ratio of phosphorylated troponin T to total troponin T as well as the level of glycosylated troponin T corresponds to the ratio of glycosylated troponin T to total troponin T.

Typically, an increased level of phosphorylated troponin T corresponds to 150% or more of the level measured in a control sample.

According to the invention, the phosphorylated troponin T is used as a biomarker of a post-infarction left ventricular remodelling in a subject.

Furthermore, the glycosylated troponin T can also be used as a biomarker of a post-infarction left ventricular remodelling in a subject.

In another embodiment of the invention, the phosphorylated troponin T is used as a biomarker of the risk of heart failure in a subject. Particularly, said subject had or not an infarction.

Furthermore, the glycosylated troponin T can also be used as a biomarker of the risk of heart failure in a subject. Particularly, said subject had or not an infarction.

Biomarkers of the invention can be detected by different methods well known in the art.

In a particular embodiment, the methods of the invention comprise contacting the biological sample with a binding partner capable of selectively interacting with the biomarkers present in the biological sample.

Accordingly, a binding partner of phosphorylated troponin T selectively recognizes the phosphorylated troponin T, and not the non-phosphorylated troponin T as well as a binding partner of glycosylated troponin T selectively recognizes the glycosylated troponin T, and not the non glycosylated troponin T.

The binding partner may be an antibody that may be polyclonal or monoclonal, preferably monoclonal. In another embodiment, the binding partner may be an aptamer.

Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred.

Monoclonal antibodies of the invention or a fragment thereof can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985).

Alternatively, techniques described for the production of single chain antibodies (see e.g. U.S. Pat. No. 4,946,778) can be adapted to produce single chain antibodies directed against biomarkers of the invention. Antibodies useful in practicing the present invention also include anti-biomarkers fragments including but not limited to F(ab')2 fragments, which can be generated by pepsin digestion of an intact antibody molecule, and Fab fragments, which can be generated by reducing the disulfide bridges of the F(ab')2 fragments. Alternatively, Fab and/or scFv expression libraries can be constructed to allow rapid identification of fragments having the desired specificity to biomarkers of the invention. For example, phage display of antibodies may be used. In such a method, single-chain Fv (scFv) or Fab fragments are expressed on the surface of a suitable bacteriophage, e.g., M13. Briefly, spleen cells of a suitable host, e.g., mouse, that has been immunized with a protein are removed. The coding regions of the VL and VH chains are obtained from those cells that are producing the desired antibody against the protein. These coding regions are then fused to a terminus of a phage sequence. Once the phage is inserted into a suitable carrier, e.g., bacteria, the phage displays the antibody fragment. Phage display of antibodies may also be provided by combinatorial methods known to those skilled in the art. Antibody fragments displayed by a phage may then be used as part of an immunoassay.

Examples of commercially available monoclonal antibodies for troponin T include those obtained from Abcam (clone 1A11, 2F3, and 1F11) and Santa Cruz (clone 2G3). Examples of commercially available polyclonal antibodies for troponin T include those obtained from HyTest Ltd (ref: 4T19_2). They are used to measure the ratio between the quantity of biomarker and the quantity of total troponin T.

In another embodiment, the binding partner may be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. 1997. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consist of conformationally constrained antibody variable regions displayed by a platform protein, such as *E. coli* Thioredoxin A, that are selected from combinatorial libraries by two hybrid methods (Colas et al., 1996).

The binding partners of the invention such as antibodies or aptamers may be labelled with a detectable molecule or substance, such as a fluorescent molecule, a radioactive molecule or any others labels known in the art. Labels are known in the art that generally provide (either directly or indirectly) a signal.

As used herein, the term "labelled", with regard to the antibody, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. For example radioactive molecules include but are not limited radioactive atom for scintigraphic studies such as I123, I124, In111, Re186, Re188.

The aforementioned assays may involve the binding of the binding partner (ie. antibody or aptamer) to a solid support. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Biomarkers of the invention may be detected by using standard immunodiagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; immunoelectrophoresis; immunoprecipitation.

More particularly, an ELISA method can be used, wherein the wells of a microtiter plate are coated with a set of antibodies directed against biomarkers of the invention. A biological sample containing or suspected of containing said biomarker(s) is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

Detecting the biomarker(s) (with or without immunoassay-based methods) may also include separation of the compounds: centrifugation based on the compound's molecular weight; electrophoresis based on mass and charge; HPLC based on hydrophobicity; size exclusion chromatography based on size; and solid-phase affinity based on the compound's affinity for the particular solid-phase that is used. Once separated, biomarkers of the invention may be identified based on the known "separation profile" e.g., retention time, for that compound and measured using standard techniques.

Alternatively, the separated compounds may be detected and measured by, for example, a mass spectrometer.

The level of total troponin T can be measured by said methods, using a binding partner which recognizes all the forms of troponin T, including phosphorylated and glycosylated troponin T.

KITS OF THE INVENTION

A further aspect of the invention provides kits comprising materials useful for carrying out predicting methods according to the present invention. The diagnosis/predicting procedures provided herein may be performed by diagnostics laboratories, experimental laboratories or practitioners. The invention provides kits that can be used in these different settings.

Material and reagents for detecting specific biomarkers of the invention in a biological sample for detecting a left ventricular remodelling or predicting a risk of heart failure in a subject may be assembled together in a kit.

In one embodiment, a kit of the invention comprises at least an antibody or other binding partner of phosphorylated troponin T and an antibody or other binding partner of troponin T, said antibody or binding partner of troponin T being able to bind all forms of troponin T.

In another embodiment, a kit of the invention comprises at least an antibody or other binding partner of phosphorylated troponin T and an antibody or other binding partner of glycosylated troponin T. The kit of the invention can also contain a binding partner of all forms of troponin T.

The binding partner can be tagged for an easier detection. It may or may not be immobilized on a substrate surface (e.g., beads, array, and the like). For example, an inventive kit may include an array for predicting the heart failure risk as provided herein. Alternatively, a substrate surface (e.g. membrane) may be included in an inventive kit for immobilization of the binding partner (e.g., via gel electrophoresis and transfer to membrane).

In addition, a kit of the invention generally also comprises at least one reagent for the detection of a complex between binding partner included in the kit and biomarker of the invention.

Depending on the procedure, the kit may further comprise one or more of: extraction buffer and/or reagents, western blotting buffer and/or reagents, and detection means. Protocols for using these buffers and reagents for performing different steps of the procedure may be included in the kit.

The different reagents included in a kit of the invention may be supplied in a solid (e.g. lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain embodiments, a kit comprises instructions for using its components for the prediction of a heart failure risk in a subject according to a method of the invention. Instructions for using the kit according to methods of the invention may comprise instructions for processing the biological sample obtained from the subject and/or for performing the test, or instructions for interpreting the results. A kit may also contain a notice in the form prescribed by a governmental agency regulating the manufacture, use or sale of pharmaceuticals or biological products.

EXAMPLES

I. Studies for Heart Failure Patients Who Had a Myocardial Infarction

Material & Methods

Animals.

All experiments performed in this study conformed to the *Guide for the care and use of laboratory animals* published by the US National Institutes of Health (NIH publication No. 85-23, revised in 1996) and with French law. Myocardial infarction (MI) was induced in 10-weeks-old male Wistar rats (n=32) (Charles River, France) by left coronary ligation according to the method described by Pfeffer et al and modified by Mulder et al. This comprised the HF (heart failure) group. Another 29 rats underwent the same protocol excepted that the snare was not tied, this was the sham-operated or control group. All rats were allowed standard rat chow and drinking water ad libitum and maintained on a 12-h/12-h light/dark cycle.

Either seven days or two months after surgery, each animal underwent hemodynamic measurements and echocardiography studies (control and HF) before sacrifice and heart removal, as recently described in Cieniewski-Bernard, C. et al, 2008. Briefly, the heart was excised and incubated in ice-cold Krebs-Henseleit buffer in order to remove blood. Each cardiac compartment was then carefully dissected to remove all the necrotic zones. The LV was immediately frozen in liquid nitrogen and kept at −80° C. until analysis. LV proteins were extracted by Dounce-Potter homogenization on ice in 40 mmol/L Tris-HCl, pH 9.5 containing anti-proteases (one tablet for 20 mL buffer, Complete™ EDTA-free, Roche Applied Science) and anti-phosphatases (1/100, Phosphatase inhibitor Cocktail 1 and 2, Sigma-Aldrich) and PUGNAc (50 μmol/L, CarboGen). The soluble fraction was transferred to 1.5 mL Eppendorf tubes and protein concentrations were determined with the Bradford assay.

Patients.

LV remodeling was analyzed in two independent populations of patients enrolled during 2002-2004 (population 1) and 2006-2007 (population 2) (Table 2). For both series of patients, inclusion criteria were hospitalization for an anterior Q-wave MI with at least 3 LV segments of the infarct zone akinetic at the predischarge echocardiography. Exclusion criteria were: inadequate echographic image quality, life-limiting noncardiac disease, significant valvular disease, or prior Q-wave MI. Serial echographic studies were performed immediately before hospital discharge and at 1 year after MI. Echographic data were obtained with commercially available second harmonic imaging systems, and images were recorded on optical disks. A standard imaging protocol was used based on apical 4- and 2-chamber views; 2D echocardiograms of the LV short axis were recorded from the left parasternal region at 3 levels: mitral valve, mid-papillary muscle level, and apex. All echocardiograms were analyzed at the Lille Core Echo Laboratory (Lille, France), as previously described in Savoye C et al, 2006[5]. LV volumes and ejection fraction were calculated according to a modified Simpson's rule. The LV was divided into a 16-segment model to evaluate regional systolic function. LV remodeling was expressed as the percentage change in LV end-diastolic volume (LVEDV) from baseline (predischarge) to 1 year afterwards: $(LVEDV_{1yr} - LVEDV_{baseline})/LVEDV_{baseline} \times 100$. Blood samples were obtained in EDTA tubes for all patients at time of inclusion during the initial hospitalization. Plasma was processed and stored at −80° C. within 2 hours.

Two-dimensional (2-D) gel electrophoresis, quantification of phosphorylated proteins and mass spectrometry analysis.

Two-dimensional gel electrophoresis was performed as previously described in Cieniewski-Bernard, C. et al, 2008. LV proteins (500 mg) from control (n=4) and HF (n=4) rats at 2 months after surgery were analyzed, mixed on a dry 24-cm strip with a pH linear gradient of 3-10 (Immobilin DryStrip, GE Healthcare). The passive rehydratation step was performed after 9 h at 20° C. without any current. Focusing was carried out at 20° C. at 50V for 9 h (active rehydration step), 200V for 1 h (linear progression), 1000V for 1 h (linear progression), 10,000V for 6 h (linear progression) and 10,000V for 4.5 h (fast progression). The equilibrated IPG strips gels were then applied to the top of a 12% Duracryl™ (Digilab® Genomic solutions) gel. Two-mm squares of filter paper containing 4 μL of PeppermintStick™Phosphoprotein Molecular Weight Standards (Molecular Probes™) were applied to the left part of the gel. Electrophoresis was performed at 10° C. with the large vertical Ettan Dalt$^{six}$ system (GE Healthcare) in running buffer (25 mmol/L Tris, 192 mmol/L glycine, 0.1% SDS (w/v), 0.37% APS (w/v) and 0.04% TEMED (v/v)) at 70V overnight.

Fluorescent staining of 2-D electrophoresis with Pro-Q®Diamond Phosphoprotein Gel Stain was performed by fixing the gels in 30% methanol (v/v), 5% acetic acid (v/v) for 2 h, washing with 18 MΩ-$H_2O$, incubating with Pro-Q®Diamond Phosphoprotein Gel Stain (Molecular Probes™) for 90 min and destaining by washing 3 times with 20% acetonitrile (ACN), (v/v), 5% sodium acetate 1 mol/L, pH 4 (w/v) for 30 min and by a final wash with 18 MΩ-$H_2O$ for 1 h. Images of Pro-Q®Diamond stained gels were acquired with an Ettan Dige Imager (GE Healthcare) at an excitation wavelength of 540 nm and an emission wavelength of 595 nm. Gels were then stained for total protein with Sypro®Ruby Protein Gel Stain (Molecular Probes™) overnight and destained by washing once with 18 MΩ-$H_2O$ for 10 min, twice with 10% methanol (v/v), 7% acetic acid (v/v) for 10 min and twice more with 18 MΩ-$H_2O$ for 10 min. Images of Sypro®Ruby stained gels were acquired with the Ettan Dige Imager at an excitation wavelength of 480 nm and an emission wavelength of 530 nm.

The images of the Pro-Q®Diamond and Sypro®Ruby stained gels were exported into TIF format and imported into ImageMaster 2D Platinum®6.0 gel image analysis software (GE Healthcare). Spots were detected automatically according to three parameters (smooth, 10; area, 5; saliency, 2). The background was removed from each gel and the images were edited manually, e.g., adding, splitting or removing spots. The Pro-Q®Diamond stained gel was chosen as the reference or master gel and used for automatic matching of spots in the corresponding Sypro®Ruby stained gel. Data analysis compared the gels for the control rats (n=4) and for the HF-rats (n=4). After manually editing and matching confirmed the images, the software analyzed the differences in protein spot volume. Total spot volume was calculated for each image, and each spot was assigned a normalized spot volume as a proportion of the total volume of all the spots. We assessed the ratio of the percentage of normalized volume of one spot detected by Pro-Q®Diamond and that for the same spot detected by Sypro®Ruby and then selected the polypeptidic spots for which this ratio differed significantly ($p<0.05$) between control and HF-rats.

As recently described in detail in Cieniewski-Bernard, C. et al, 2008 and Pottiez G et al, 2009, LV phosphoproteins (800 μg) were identified by an in-gel digestion method after staining with Coomassie Brillant Blue G-250, and the proteins were identified with a MALDI-TOF mass spectrometer Voyager DE-STR PRO (PerSeptive Biosystems) and, for the spots not identified in MALDI, with the Proteineer™ workflow from Bruker Daltonics (Bremen, Germany).

Monoisotopic peptides masses were sought in the NCBI and Swiss-Prot proteins databases with three separate software programs: Protein Prospector, ProFound and Mascot. The databases searches used different characteristics, i.e. rat species, one missed cleavage, partial chemical modifications (oxidation of methionine and carbamidomethylation of cysteine) and a mass tolerance setting of 50 ppm. Criteria used to accept the identifications included the probability score, the number of matched peptides (minimum of 4 peptides), the extent of sequence coverage (>20%) and the molecular weight and isoelectric point of the proteins identified.

Immunoprecipitation and Western Blot Analysis.

Immunoprecipitation was performed with 25 or 50 μg of LV proteins or 1 μL of plasma mixed with 1 μg of antibody diluted in RIPA buffer (10 mmol/L Tris HCL, 150 mol/L NaCl, 10% IGEPAL® CA-630 (Sigma-Aldrich) (v/v), 0.5% sodium deoxycholate (w/v), 10% SDS (w/v), and 10% sodium orthovanadate (w/v)). After incubation at 4° C. overnight on a rotating device, immune complexes were precipitated at 4° C. for 1 h on a rotating device with nProtein A Sepharose™ 4 Fast Flow (GE Healthcare). Immunoprecipitates were first washed with RIPA buffer, then with 90% RIPA buffer (v/v), NaCl 0.5 mol/L, then with 50% RIPA buffer (v/v), 50% TNE buffer (v/v) (10 mmol/L Tris HCl, 150 mmol/L NaCl, 1 mmol/L EDTA) and finally with TNE buffer before extraction in Laemmli buffer for western blot analysis.

Proteins (25 to 50 μg LV or 1 μL from plasma) from LV were separated by SDS-PAGE (12% acrylamide gel) and transferred onto 0.45 μm Hybond™ nitrocellulose membrane (GE Healthcare). Verification of total protein loads was confirmed visually by Ponceau red staining of the membrane. The blots were then washed in TBS-Tween, saturated in 5% non fat dry milk or BSA (w/v) in TBS-Tween and were blotted overnight in blocking solution with antibodies against specific proteins. The primary antibodies were against phosphoserine residues (monoclonal p-serine antibody, clone PSR-45, P5747, Sigma-Aldrich, before or after immunoprecipitation), phosphothreonine residues (monoclonal p-threonine antibody, clone H-2, sc-5267, Santa Cruz Biotechnology®, before or after immunoprecipitation), protein kinase C alpha (polyclonal PKCα antibody, AHO0702, Invitrogen™, 50 μg proteins/lane, 1/250), protein kinase C delta (monoclonal PKCδ antibody, clone ZP012, 41-0300, Invitrogen™, 50 μg, 1/250), protein kinase C epsilon (polyclonal PKCε antibody, AHO0743, Invitrogen™, 50 μg, 1/1000), troponin I (polyclonal troponin I antibody, #4002, Cell Signaling Technology®, 25 μg, 1/1000), troponin I phosphorylated on S23/24 (polyclonal phosphotroponin I antibody, #4004, Cell Signaling Technology®, 25 μg, 1/500), troponin T (monoclonal troponin T-C antibody, clone 2G3, sc-33721, Santa Cruz Biotechnology®, 50 μg before or after immunoprecipitation, 1/100) and O-GlcNAc moieties (Covance, 50 μg or after IP, 1/1000). The blots were then washed five times in TBS-Tween for 10 min each and then incubated with horseradish peroxidase labeled secondary antibody for 1 h in blocking solution. The secondary antibodies were ECL™ anti-rabbit IgG horseradish peroxidase linked whole antibody from donkeys (NA934V, GE Healthcare) and ECL™ anti-mouse IgG horseradish peroxidase linked whole antibody from sheep (NA931V, GE Healthcare). Membranes were washed five times in TBS-Tween for 10 min each. The blots were then incubated with enhanced chemiluminescence (ECL™) western blotting detection reagents (GE Healthcare). The Ettan DIGE Imager (GE Healthcare) was used for detection, with an excitation wavelength of 480 nm and an emission wavelength of 530 nm. The intensity of the bands was quantified with Quantity One® Image analyzer software (Bio-Rad).

Troponin T and Phospho-Troponin T Specific Antibodies.

Anti-peptide polyclonal antibodies against the 202-215 conserved sequence of rat troponin T, specific for either TnT or phosphorylated $Ser^{208}$-TnT, were developed according to a standard protocol (immunization of 3 months, P.A.R.I.S society, France). Polyclonal antibodies were purified against the phosphorylated $Ser^{208}$- and non phosphorylated TnT peptides to test for recognition of each form of troponin T. The polyclonal antibodies were purified for all the experiments. To test the specificity of the antibodies, 50 μg of LV proteins was treated with 50 and 100 units of alkaline phosphatase (M0290S, New England Biolabs) for 18 hours at 37° C. Proteins were then separated by SDS-PAGE (12% acrylamide gel), transferred onto PVDF membranes and blotted overnight in blocking solution with antibodies against either $Ser^{208}$-phosphorylated TnT or TnT (1/1000) pre-incubated with phosphorylated or non-phosphorylated $Ser^{208}$ peptides (202-215 aa) at a final concentration of 10 μg/mL. Western blot analyses with the purified polyclonal antibodies were performed as described above with 50 μg of LV proteins or 1 μL of rat or human plasma.

Statistical Analysis.

Continuous variables are expressed as mean±SD unless otherwise indicated. Differences in LVED (1 year versus baseline) were assessed by the paired Student's t test. Differences between groups were compared by an unpaired bilateral Student's t test or by ANOVA followed by a Scheffe's F procedure for post hoc comparisons. A value of p<0.05 was considered statistically significant.

Results

Differential Phosphoproteomic Analysis of the Left Ventricle in Control and Heart Failure Model Rats at 2 Months after Surgery.

This study investigated cardiac phosphoproteome changes in LV remodeling and dysfunction in an experimental model of MI induced by ligation of the left coronary artery in HF-rats and sham-operated (control) rats. Detailed echocardiographic, hemodynamic and histomorphometric parameters were measured in anesthetized rats 7 days and 2 months after surgery.

At 2 months, proteomic analysis revealed different LV phosphoproteome patterns between the groups, with 32±5 and 52±8 phosphorylated spots detected (p=0.013) in control and HF rats, respectively, although their LV proteome patterns were similar (309±49 and 284±29 spots). Using the 2D-gel containing the most spots, we selected 69 spots differentially phosphorylated between the groups; 53 of them could be identified by mass spectrometry. These proteins were classified in 8 categories according to their functional significance: molecular chaperones, proteins of oxidative stress, metabolic enzymes, proteins of the respiratory chain, proteins implicated in ATP synthesis or in the kinin pathway or in regulation of colloidal osmotic blood pressure, and finally several myofilaments components.

In the latter category, the finding that troponin T (TnT) phosphorylation was modified was especially interesting. TnT itself is a well-established biomarker in cardiovascular diseases, and elevated levels of serum TnT are associated with altered clinical outcomes in conditions including MI (Newby, L K et al, 1998) and HF (Latini R et al, 2007). We therefore explored the process of decreased TnT phosphorylation in HF in greater depth.

Decreased Troponin T Phosphorylation in the LV of HF Rats.

To verify the observation of decreased TnT phosphorylation in 2D-gel electrophoresis experiments, we next determined its specific amino acid site of protein phosphorylation and the extent to which TnT phosphorylation was modulated during the HF course in the 2 months after the MI.

By immunoprecipitation with a specific antibody against TnT followed by western blot analysis with phospho-serine (Ser), -threonine (Thr) or -tyrosine (Tyr) antibodies, we determined that TnT was phosphorylated on Ser- and Thr-residues. The extent of phosphorylation on TnT Ser-residues in the LV of HF rats after 2 months decreased significantly, while we observed no significant modulation of phosphorylation on TnT Thr-residues. In addition, total TnT expression did not differ between control and HF rats. Similar results were observed in HF rats 7 days after MI: phosphorylation on TnT Ser-residues decreased significantly.

To confirm that the modulation of phosphorylation was specific to TnT, we performed western blot analysis of the same samples, using specific antibodies against either troponin I (TnI) or $Ser^{23/24}$ phosphorylated TnI, in view of the suggestion that reduced TnI phosphorylation of $Ser^{23/24}$ might account for the functional difference between failing and non failing heart troponin (Messer A E et al, 2007). In our model, we observed no variation in the expression of either TnI or $Ser^{23/24}$ phosphorylated TnI in HF rats or control rats, 7 days or 2 months after surgery.

We then investigated the signalling proteins associated with the modulation of TnT Ser-phosphorylation. Bioinformatical analysis (NetPhos 2.0 Server, PhosphoSitePlus™ and Scansite) suggested that only serine at position 208 (in the rat TnT sequence) could be phosphorylated, and that the amino acids surrounding $Ser^{208}$ were consensus sites for protein kinase C (PKC) and for protein phosphatase 2A ($PP_2A$).

Decrease in $Ser^{208}$-Phosphorylated Troponin T in the LV and Plasma of HF Rats, Assessed with Specific Antibodies.

We synthesized the phosphopeptide, including amino acid residues 202-215 of the rat TnT sequence (1-298 aa), with phosphorylated $Ser^{208}$. This amino acid sequence is highly conserved among human ($Ser^{207}$), mouse ($Ser^{210}$), rabbit ($Ser^{210}$) and cow ($Ser^{194}$) species. Polyclonal antibodies were raised against the peptide sequence and purified against both the phosphorylated and non-phosphorylated TnT peptides, and their specificities were studied. Both antibodies detected TnT from rat LV at 34 kDa. We characterized the specificity of the antibody for the $Ser^{208}$-phosphorylated form of TnT with both the $Ser^{208}$-phosphorylated and non phosphorylated peptides. Antibody binding was abolished only with the $Ser^{208}$-phosphorylated peptide. In contrast, binding of the antibody purified against the non-phosphorylated peptide was abolished by incubation with both peptides; this indicates that this antibody recognized total TnT and not only its non-phosphorylated form. For further confirmation of the antibody's specificity for $Ser^{208}$-phosphorylated TnT, we treated LV proteins with alkaline phosphatase to remove all phosphate moieties. Again, antibody binding was abolished.

Next, we examined the antibody's cross-reactivity with other troponins for $Ser^{208}$-phosphorylated TnT. The corresponding TnI sequence had 5/14 amino acids in common with rat TnT and 0/14 with human, and serine residues were absent in both species. We also used specific antibodies for immunoprecipitation of total or $Ser^{23/24}$-phosphorylated TnT from LV proteins. Western blot analysis with $Ser^{208}$-phosphorylated and total TnT antibodies produced no signal and thus demonstrated a lack of cross-reactivity with TnI.

Next, we used these specific antibodies for $Ser^{208}$-phosphorylated TnT and for total TnT, to quantify precisely the degree of $Ser^{208}$-phosphorylation of TnT in HF rats, and to confirm the data obtained by indirect methods. Using the antibody against total TnT, we found no modification of TnT expression in the LV of HF rats at 2 months and confirmed the decreased level of the $Ser^{208}$-phosphorylated form of TnT in their LV. The ratio of $Ser^{208}$-phosphorylated TnT to total TnT was thus significantly lower in these rats. Results were similar for HF rats at 7 days.

We next investigated whether the modulation of $Ser^{208}$-phosphorylation of TnT could also be detected and quantified in the plasma of HF rats. Total TnT was modestly (by a factor of 1.7) but significantly increased in the plasma of the HF rats at 2 months, and as in the LV, we observed a significant decrease of $Ser^{208}$-phosphorylated TnT in their plasma. Results were similar for the HF rats at 7 days. At both time points, the $Ser^{208}$-phosphorylated TnT to total TnT ratio quantified in plasma was significantly lower in HF than in control rats.

Decrease in Human $Ser^{207}$-Phosphorylated Troponin T in Plasma of Patients with LV Remodelling.

Our finding of a specific decrease of $Ser^{208}$-phosphorylated TnT in the plasma of rats with HF after MI suggested that circulating phosphorylated TnT might be a biomarker of LV remodeling in MI patients. Because our polyclonal antibodies also specifically recognized the human $Ser^{207}$-phosphorylated TnT sequence, we quantified circulating phosphorylated TnT in 2 different populations of patients with anterior MI. Complete echocardiographic follow-up was obtained for most patients throughout the first year post-MI. In both populations, a progressive increase in LV volume from baseline to 1 year indicated LV remodeling. The remodeling process occurred despite nearly systematic use of anti-remodeling medications including angiotensin-converting enzyme inhibitors and betablockers.

Figure 1B:
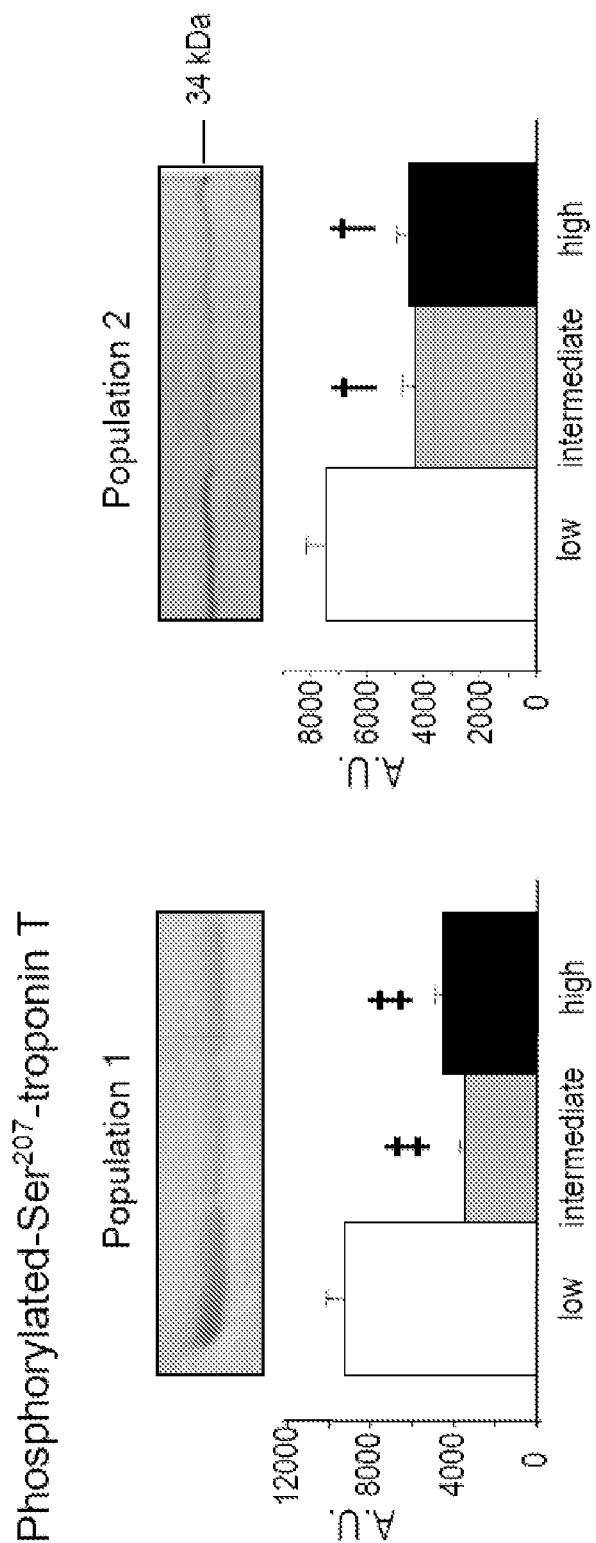
FIG. 1B depicts western blot analysis with antibodies against the human $Ser^{207}$-phosphorylated TnT in plasma (1 µL) from patients.
Figure 1C:
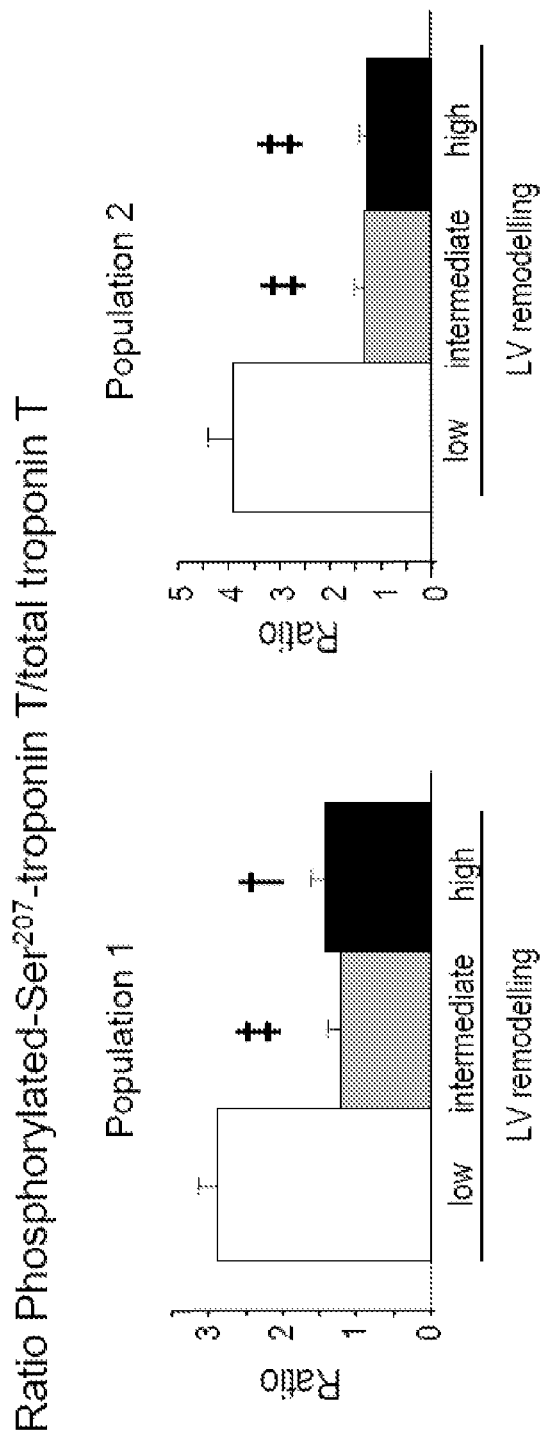
FIG. 1C shows analysis of the ratio between total human TnT and human $Ser^{207}$-phosphorylated TnT. The positions of Mw are indicated on the right in FIGS. 1A and 1B. Total human TnT and $Ser^{207}$-phosphorylated TnT were quantified in 2 independent populations (named population 1 and population 2). Each population was divided into tertiles according to percentage of LV remodelling, measured as indicated in materials and methods. Tertile 1 includes patients with low remodelling (white box), tertile 2 represents patients with intermediate remodelling (grey box) and tertile 3 represents patients with a high degree of remodelling (black box). Data are expressed as means of an arbitrary unit (A.U.).±SEM. †p<0.001, ‡p<0.0001.

Blood samples for TnT analysis were obtained at 7±3 days after MI in population 1, and at 5±1 days after MI in population 2. Patients were divided into tertiles of LV remodeling according to their LV end diastolic volumes, measured one year after MI; the first tertile comprised the patients with the least remodeling, the second tertile those with intermediate remodeling, and the third tertile, those with the most remodeling. Use of anti-remodeling medications was similar among the 3 groups. As FIG. 1 shows, total TnT expression in population 1 did not differ in the LV remodeling tertiles, while in population 2 we observed a moderate but non-significant increase in total TnT expression in patients with intermediate and high remodeling. $Ser^{207}$-phosphorylated TnT decreased significantly in both populations and the $Ser^{207}$-phosphorylated TnT/total TnT ratio decreased very significantly in patients with intermediate or high remodeling. This finding was similar in the 2 independent patient populations.

The Relationship Between the Phosphorylated Troponin T/Total TnT Ratio and the Percentage Change in End-Diastolic Volume (EDV).

Continuous variables are expressed as mean±SD or as median with $25^{th}$ and $75^{th}$ percentiles unless otherwise indicated. Variables that did not follow normal distribution were log transformed prior to statistical testing. Differences in EDV (1 year versus baseline) were assessed by the paired Student's t test. Differences between groups were compared by an unpaired bilateral Student's t test or by ANOVA followed by Scheffe's F procedure for post hoc comparisons. Categorical data were tested by the Chi-square test or the Fischer's exact test as appropriate. The relationship between the percentage change in EDV and the ratio of $Ser^{207}$-phosphorylated TnT to total TnT was tested by linear regression. Independent correlates of change in EDV were identified by multiple linear regression. Variables with a p value <0.05 on univariate analysis were entered into the model. Colinearity was excluded by means of a correlation matrix between candidate predictors. A value of p<0.05 was considered statistically significant. Analyses were performed with SAS software (release 9.1, SAS Institute Inc., Cary, N.C., USA).

Blood samples for biological analysis were obtained at 7±3 days after MI. Total TnT expression in the population did not differ in the LVR tertiles. $Ser^{207}$-phosphorylated TnT and its ratio to total TnT decreased very significantly in patients with intermediate or high remodelling.

The relationship between this ratio and the percentage change in EDV between baseline and 1 year (expressed as a continuous variable) was analyzed by linear regression and found to be statistically significant (p=0.0003). Multivariable analyses to determine independent correlation of LVR found three variables independently associated with the change in EDV: the ratio of $Ser^{207}$-phosphorylated TnT to total TnT (p=0.002), the wall motion systolic index (p=0.002), and hypertension (p=0.045).

|  | Standardized β coefficient | P value |
|---|---|---|
| $Ser^{207}$-phosphorylated TnT to total TnT ratio | −0.308 | 0.002 |
| Wall motion systolic index | 0.292 | 0.002 |
| Hypertension | 0.194 | 0.045 |
| Diabetes mellitus | 0.005 | 0.955 |

Increase in O-GlcNAcylation Troponin T in the LV and Plasma of HF Rats.

By immunoprecipitation with a specific antibody against TnT followed by a western blot analysis with O-GlcNAc moieties antibody, we observed a significant increase of O-GLcNAc-TnT in the left ventricule of HF rats after 7 days (p=0.0023) and 2 months (p=0.0000004).

We next investigated whether the modulation of O-GLcNAc-TnT could also be detected and quantified in the plasma of HF rats. We also observed a significant increase of O-GLcNAc-TnT in plasma of HF rats after 7 days (p=0.012) and 2 months (p=0.0004).

We can hypothesize an interplay between O-GlcNAcylation and phosphorylation of Troponin T in HF rats.

II. Studies for Heart Failure Patients Who Had No Infarction

The PTHF Protocol.

The ProTeomic Heart Failure (PTHF) is a clinical study including 30 patients suffering from severe heart failure due to systolic dysfunction (left ventricular ejection fraction <35%) sent to the cardiology department for a prognostic assessment of a non-ischemic dilated cardiomyopathy. The control group is made up of 30 controls selected by the CIC-CRB of the CHRU of Lille from a base of healthy volunteers. These age and sex-matched controls for the group of patients suffering from heart failure were subject to a cardiac examination and ultrasound scanning by a cardiology investigator.

Using our specific polyclonal antibodies and western blot analysis, we have quantified the level of total troponin T, phosphorylated $Ser^{207}$-Troponin T and calculated the ratio phosphorylated $Ser^{207}$-Troponin T on total troponin T. Data obtained from the control and case patients are shown below.

|  | Control (n = 30) | Case (n = 30) |
|---|---|---|
| Total troponin T | 2556 ± 223 | 2583 ± 237 |
| Phosphorylated $Ser^{207}$-Troponin T | 10286 ± 485 | 9547 ± 502 |

These results show that phosphorylated troponin T can be used as a biomarker of left ventricular remodelling but also of heart failure (in case or not of infarction). Glycosylated troponin T also appears to be indicative of such mechanisms and can be used to precise and confirm the results obtained with phosphorylation of troponin T.

Plasma Levels of Troponin T-OGlCNAc are Increased in Case Patients from PTHF Study.

Immunoprecipitation was performed with 1 μL of plasma mixed with 1 μg of antibody diluted in RIPA buffer (10 mmol/L Tris HCL, 150 mol/L NaCl, 10% IGEPAL® CA-630 (Sigma-Aldrich) (v/v), 0.5% sodium deoxycholate (w/v), 10% SDS (w/v), and 10% sodium orthovanadate (w/v)). After incubation at 4° C. overnight on a rotating device, immune complexes were precipitated at 4° C. for 1 h on a rotating device with nProtein A Sepharose™ 4 Fast Flow (GE Healthcare). Immunoprecipitates were first washed with RIPA buffer, then with 90% RIPA buffer (v/v), NaCl 0.5 mol/L, then with 50% RIPA buffer (v/v), 50% TNE buffer (v/v) (10 mmol/L Tris HCl, 150 mmol/L NaCl, 1 mmol/L EDTA) and finally with TNE buffer before extraction in Laemmli buffer for western blot analysis.

Proteins (1 μL from plasma) were separated by SDS-PAGE (12% acrylamide gel) and transferred onto 0.45 μm Hybond™ nitrocellulose membrane (GE Healthcare). Total protein load was confirmed visually by Ponceau red staining of the membrane. The blots were then washed in TBS-Tween, saturated in 5% non fat dry milk or BSA (w/v) in TBS-Tween and were blotted overnight in blocking solution with antibodies against specific proteins. The primary antibodies used were O-GlcNAc moieties (mouse monoclonal O-GlcNAc antibody, clone CTD110.6, MMS-248R-0500, Covance, for IP). The secondary antibodies used for western blot analysis were ECl™ anti-mouse IgG horseradish peroxidase linked whole antibody from sheep (NA931V, GE Healthcare) and anti-mouse IgM peroxidase conjugate from goat (A8786, Sigma-Aldrich).

The specificity of western blot of O-GlcNAc proteins was controlled by enzymatic digestion. One μL of plasma was treated with 100 units of alkaline phosphatase (M0290S, New England Biolabs®) diluted in enzyme buffer or with 15 units of β-N-Acetylhexosaminidase$_f$ (P0721S, New England Biolabs®) dilute in citrate buffer 100 mM during 18 hours at 37° C. to remove all phosphorylated or O-GlcNAc residues.

The intensity of the bands was quantified with Quantity One® Image analyzer software (Bio-Rad) as detailed below: 1) a square with a defined size was used for quantification of each band detected as well for the background of the membrane; 2) for each band corresponding to LV samples, the background value was deduced from the intensity value; 3) the intensity value of each sample was normalized to the value of standard to eliminate variation between blots.

Plasma proteins (1 uL) were immunoprecipitated using specific antibody against O-GlcNAc moieties and subjected to western blot against cTnT of control (n=30) and case (n=30) patients from PTHF study.

|  | Control (n = 30) | Case (n = 30) |
|---|---|---|
| Total troponin T | 2556 ± 223 | 2583 ± 237 |
| Troponin T-O-GlcNAc | 2838 ± 260 | 3875 ± 339 |

REFERENCES

Throughout this application, various references describe the state of the art to which this invention pertains. The disclosures of these references are hereby incorporated by reference into the present disclosure.

Brummelkamp T R, Bernards R, Agami R. "A system for stable expression of short interfering RNAs in mammalian cells." Science. 2002; 296(5567):550-3.

Chen C H, Gray M O, Mochly-Rosen D. Cardioprotection from ischemia by a brief exposure to physiological levels of ethanol: role of epsilon protein kinase C. Proc Natl Acad Sci USA. 1999; 96(22):12784-9.

Cieniewski-Bernard, C. et al. Proteomic Analysis of left ventricular remodeling in an experimental model of heart failure. *J. Proteome Res.* 7, 5004-5016 (2008).

Colas P, Cohen B, Jessen T, Grishina I, McCoy J, Brent R: Genetic selection of peptide aptamers that recognize and inhibit cyclin-dependent kinase 2. Nature 380:548-550, 1996.

Cole et al. "Monoclonal Antibodies and Cancer Therapy", Alan R. Liss, Inc., 1985, pp. 77-96.

Cote R J, Morrissey D M, Houghton A N, Beattie E J, Jr., Oettgen H F, Old L J: Generation of human monoclonal antibodies reactive with cellular antigens. Proc Natl Acad Sci USA 80:2026-2030, 1983

Elbashir S M, Martinez J, Patkaniowska A, Lendeckel W, Tuschl T. "Functional anatomy of siRNAs for mediating efficient RNAi in *Drosophila melanogaster* embryo lysate". The Embo Journal. 2001; 20(23):6877-88.

Hannon G J. "RNA interference." Nature. 2002; 418(6894):244-51.

Köhler G, Milstein C. "Continuous cultures of fused cells secreting antibody of predefined specificity". Nature. 1975; 256(5517):495-7.

Latini, R. et al. Pronostic value of very low plasma concentrations of troponin T in patients with stable chronic heart failure. *Circulation* 116, 1242-1249 (2007).

McManus M T, Haines B B, Dillon C P, Whitehurst C E, van Parijs L, Chen J, Sharp P A. "Small interfering RNA-mediated gene silencing in T lymphocytes." Journal of Immunology. 2002; 169(10):5754-60.

Messer, A. E., Jacques, A. M. & Marston S B. Troponin phosphorylation and regulatory function in human heart muscle: dephosphorylation of Ser23/24 on troponin I could account for the contractile defect in end-stage heart failure. *J. Mol. Cell. Cardiol.* 42, 247-249 (2007).

Mulder, P. et al. Role of endogenous endothelin in chronic heart failure: effect of long-term treatment with an endothelin antagonist on survival, hemodynamics, and cardiac remodeling. *Circulation* 96, 1976-1982 (1997).

Newby, L. K. et al. Value of serial troponin T measures for early and late risk stratification in patients with acute coronary syndrome. The GUSTO-IIa Investigators. *Circulation* 98, 1853-1859 (1998).

Pfeffer, M. A., Pfeffer, J. M., Steinberg, C. & Finn, P. Survival after an experimental myocardial infarction: beneficial effects of long-term therapy with captopril. Circulation. 72, 406-412 (1985).

Pottiez, G., Sevin, F., Ceccheli, R., Karamanos, Y. & Flahaut C. Actin, gelsolin and filamin-A are dynamic actors in the cytoskeleton remodelling contributing to the blood brain barrier phenotype. Proteomics 9, 1207-1219 (2009).

Savoye, C. et al. Left ventricular remodeling after anterior wall acute myocardial infarction in modern clinical practice (from the REmodelage VEntriculaire [REVE] study group). *Am. J. Cardiol.* 98, 1144-1149 (2006).

Tuerk C, Gold L. "Systematic evolution of ligands by exponential enrichment: RNA ligands to bacteriophage T4 DNA polymerase". Science. 1990; 249(4968):505-10.

Tuschl T, Zamore P D, Lehmann R, Bartel D P, Sharp P A. "Targeted mRNA degradation by double-stranded RNA in vitro". Genes & development, 1999; 13(24):3191-7.

The invention claimed is:

1. An in vitro method for predicting the risk of heart failure in a human subject who had an infarction, said method comprising the steps of:
   (i) measuring the level of troponin T phosphorylated on serine 207 in the troponin T pool in a blood sample obtained from the subject by an ELISA immunoassay consisting of:
      providing a microtiter plate coated with a set of antibodies specific for troponin T phosporylated on serine 207;
      adding the blood sample to the coated wells;
      washing the plate after a period of incubation sufficient to allow the formation of antibody-antigen complexes to remove unbound moieties;
      adding a detectably labelled secondary binding molecule which is allowed to react with any captured sample marker protein;
      washing the plate; and
      detecting the presence of the secondary binding molecule,
   (ii) comparing said measured level of troponin T phosphorylated on serine 207 to a control level of troponin T phosphorylated on serine 207 obtained from a healthy subject,
   (iii) wherein when the level of troponin T phosphorylated on serine 207 determined at step i) is lower than the control level of troponin T phosphorylated on serine 207, it is indicative of a high risk of heart failure.

2. The method of claim 1, wherein said method comprises the further steps of:
   (iv) measuring the level of glycosylated troponin T in the troponin T pool in said blood sample,
   (v) comparing said level to a control level obtained from a healthy subject,
   (vi) wherein when the level determined at step i) is higher than the control level it is indicative of a high risk of heart failure.

* * * * *